(12) United States Patent
Cooper et al.

(10) Patent No.: US 7,836,081 B2
(45) Date of Patent: Nov. 16, 2010

(54) EVENT NOTIFICATION VERIFICATION AND ESCALATION

(75) Inventors: Gregory Cooper, Santa Ana, CA (US); Albert A. Hernandez, Tustin, CA (US); Wilhelmina Bowman Maloles, Cerritos, CA (US)

(73) Assignee: Compressus, Inc., Washington, DC (US)

( * ) Notice: Subject to any disclaimer, the term of this patent is extended or adjusted under 35 U.S.C. 154(b) by 306 days.

(21) Appl. No.: 11/233,776

(22) Filed: Sep. 22, 2005

(65) Prior Publication Data

US 2007/0067363 A1 Mar. 22, 2007

(51) Int. Cl.
*G06F 17/30* (2006.01)
(52) U.S. Cl. .................. 707/791; 706/1; 706/2; 706/3; 706/4; 706/5
(58) Field of Classification Search .......... 707/640, 707/791; 706/1–6
See application file for complete search history.

(56) References Cited

U.S. PATENT DOCUMENTS

| 5,706,452 | A | 1/1998 | Ivanov | |
|---|---|---|---|---|
| 7,272,610 | B2 * | 9/2007 | Torres | 707/101 |
| 2002/0107958 | A1 * | 8/2002 | Faraldo, II | 709/224 |
| 2003/0220815 | A1 * | 11/2003 | Chang et al. | 705/2 |
| 2004/0088313 | A1 | 5/2004 | Torres | |
| 2005/0010463 | A1 * | 1/2005 | Du et al. | 705/8 |
| 2006/0259524 | A1 * | 11/2006 | Horton | 707/201 |
| 2007/0162973 | A1 * | 7/2007 | Schneier et al. | 726/22 |

OTHER PUBLICATIONS

International Search Report and the Written Opinion of the International Searching Authority for PCT/US06/36755 dated Mar. 10, 2008.

* cited by examiner

*Primary Examiner*—Cam Y Truong
*Assistant Examiner*—Noosha Arjomandi
(74) *Attorney, Agent, or Firm*—The Marbury Law Group PLLC

(57) ABSTRACT

Documents to be accessed over a computer network are stored in network data storage such that each document is associated with a document archive and a task is associated with each stored document. An escalation list is created for each task and is associated with the document archive so as to specify an ordered list of escalation items to be satisfied until fulfillment of the task. When a parameter associated with each escalation list item has been satisfied, process operations associated with the next escalation list item are performed. Fulfillment of the task results in appending a verification of task fulfillment to the document archive.

22 Claims, 7 Drawing Sheets

| Document No. 987654 | |
|---|---|
| Patient name | John Subject |
| Study | Knee 2005 Jan 01 |
| Series | series 1 |
| Image | image 1 |
| Instance | frame 1, 2005 Jan 01, lateral |
| | frame 2, 2005 Jan 01, anterior |
| | frame 3, 2005 Jan 01, medial |

402

| Document No. 987654 | Report for John Subject | Patient no. 23456 |
|---|---|---|
| Study 23, Series 1. | | |
| ACTION | CONTACT DATA | EXPIRATION TIME |
| Call mobile phone | 101-555-7654 | 30 minutes |
| call pager | 101-555-2345 | 15 minutes |
| call business office | 888-555-9234 | 3 minutes |
| send email message (with attachment) | notify@hospital.com<br>c:\docs\details_note.doc | 2 minutes |
| call answering service | 800-555-1111 | 2 minutes |
| call colleague | | |
| call administrator | | |
| send fax (document) | | |
| send email message | | |
| request human intervention | | |

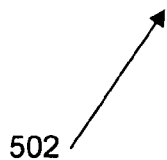

| Document No. 987654 | |
|---|---|
| Patient name | John Subject |
| Study | Knee 2005 Jan 01 |
| Series | series 1 |
| Image | image 1 |
| Instance | frame 1, 2005 Jan 01, lateral |
| | frame 2, 2005 Jan 01, anterior |
| | frame 3, 2005 Jan 01, medial |
| Task History | |
| Received | 2005 Jan 01 4:30 pm |
| Received from | Imaging Lab |
| Reviewed | 2005 Jan 02 9:15 am |
| Reviewed by | John Expert, MD |

602

EVENT NOTIFICATION VERIFICATION AND ESCALATION

CROSS REFERENCE TO RELATED APPLICATIONS

This application is related to co-pending U.S. patent application Ser. No. 11/233,777, filed Sep. 22, 2005, entitled "Method and Apparatus for Boundary-Based Image Compression", U.S. patent application Ser. No. 11/233,778, filed Sep. 22, 2005, entitled "Method and Apparatus for Adjustable Image Compression", and U.S. patent application Ser. No. 11/233,775, filed Sep. 22, 2005, entitled "Autonomous Routing of Network Messages", all of which are incorporated by reference.

BACKGROUND OF THE INVENTION

1. Field of the Invention

This invention relates generally to processing of documents that are accessed over computer networks and, more particularly, to notification of network events involving such documents.

2. Description of the Related Art

Computer document processing systems typically receive documents for storage and place the documents in network data storage for retrieval by network users. The document processing is an important function that must be carefully and efficiently performed. For example, a health care delivery system at a facility such as a hospital or medical center will receive and store documents of many different types. It is critical for the health of patients that documents are delivered to appropriate medical staff, with no loss of information. Some document processing systems are integrated with message handling functions. The documents may be received, for example, as attachments to messages. A hospital computer network may have the capability to process documents and messages of different message types. For example, an integrated hospital document processing system might have the capability of storing telephone messages, email or other electronic messages, and also documents, with functionality for data distribution, storage, and access among the different offices or laboratories of the hospital. Other facilities have similarly varied and stringent requirements for processing incoming documents and managing access to them.

Many of the documents (and the messages that often accompany or bring such documents to the facility) must be reviewed, studied, or otherwise handled by facility personnel. In the hospital setting, such personnel can include physicians, specialists, medical support staff, and administrative support staff. In addition, documents might be received from, or might need to be handled by or provided to, outside personnel, such as laboratory personnel, clinicians, governmental agency personnel, suppliers, and the like. Document processing systems for other facilities can have a similarly varied array of persons who need to handle documents and also provide such documents.

With the advent of data access, privacy, and management requirements imposed by regulations (such as the Health Insurance Portability and Accountability Act of 1996 in the U.S.A., referred to as HIPAA) and the like, it is becoming increasingly important for document processing systems to carefully control access to documents, and carefully archive processed documents for later access. Such regulatory schemes often have stringent requirements for proof of timely action in response to received documents. It is therefore important for a document processing system to provide verification of proper document processing and timely handling.

It would be advantageous if a document processing system could automatically provide for needed verification of document processing and also assist in ensuring that appropriate personnel have performed their assigned document tasks.

From the discussion above, it should be apparent that there is a need for a document processing system that can provide verification of document processing tasks and can assist personnel in ensuring appropriate document handling. The present invention fulfills this need. Other problems with the prior art not described above can also be overcome using the teachings of the present invention, as would be readily apparent to one of ordinary skill in the art after reading this disclosure.

SUMMARY

Documents to be accessed over a computer network are stored in network data storage such that each document is associated with a document archive and a task is associated with each stored document, and an escalation list is created and is associated with the document archive so as to specify an ordered list of notification items to be performed in fulfillment of the task. When a parameter (e.g., a time limit) associated with each escalation list item has been satisfied, process operations associated with the next escalation list item are performed, and otherwise fulfillment of the task results in appending a verification of task fulfillment to the document archive. The escalation list can include contact information, such as telephone contact data for a plurality of telephone numbers, or network address locations to which a network message can be sent. The last process operation associated with the escalation list can be a request for human intervention that requires a physical acknowledgment action by a human operator to be deemed fulfilled, such as a human input from a system input/output device. This helps ensure that otherwise unfulfilled tasks will eventually receive attention and do not go unfulfilled.

Other features and advantages of the present invention should be apparent from the following description of exemplary embodiments, which illustrate, by way of example, the principles of the invention.

BRIEF DESCRIPTION OF THE DRAWINGS

FIG. 5 is a representation of an escalation list data structure that is stored in the system illustrated in FIG. 1.

DETAILED DESCRIPTION

System Configuration

Figure 1:
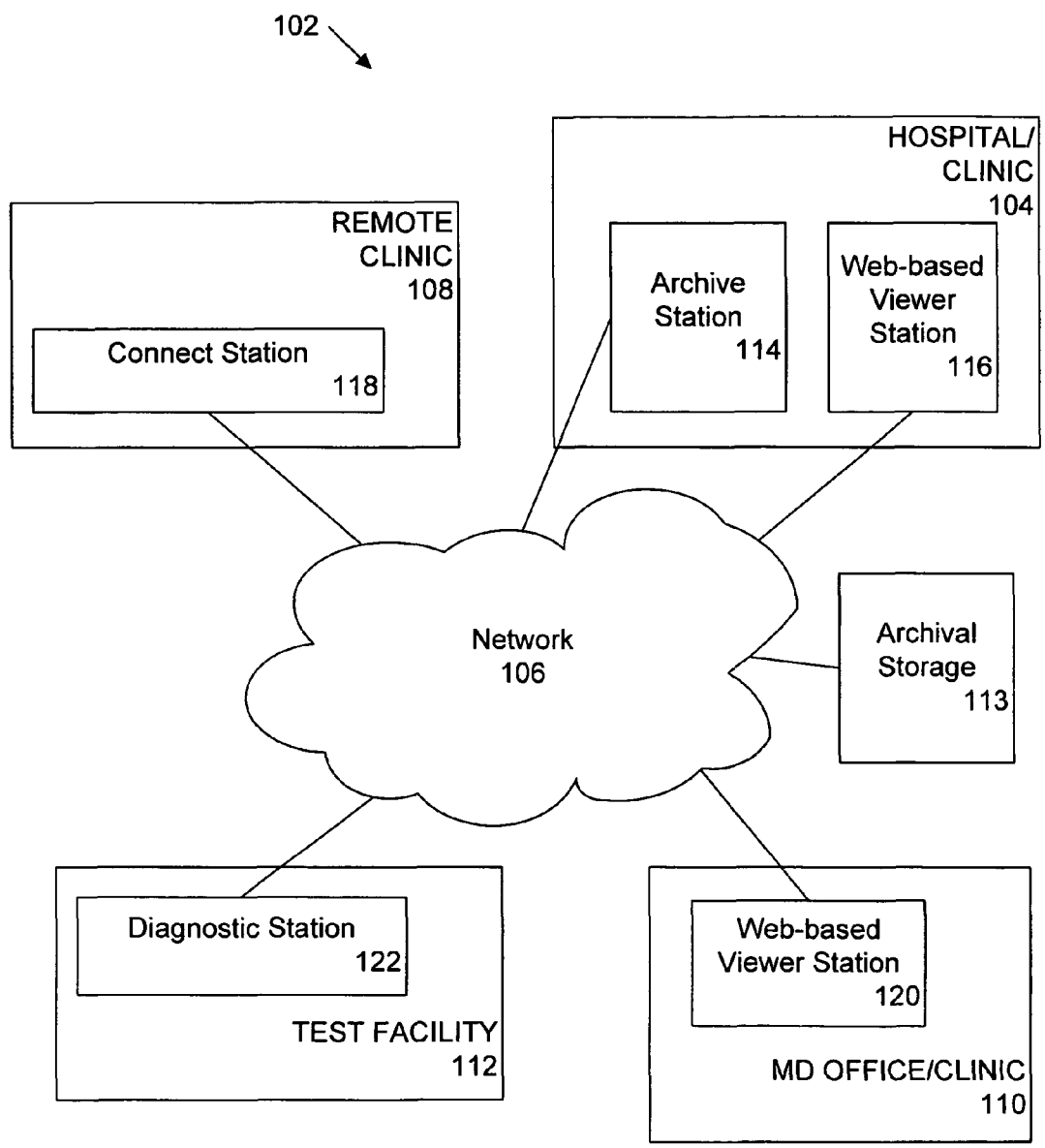
FIG. 1 is a block diagram that shows a document processing system constructed in accordance with an embodiment of the invention.

FIG. 1 is a block diagram representation of a computer system 102 in which documents and messages are exchanged among network locations and documents are stored and maintained in a network data store with automatic event notification verification and escalation. A facility with document processing, such as a hospital or central clinic 104, communicates over a network 106 with other document processing facilities, such as a remote clinic 108, medical doctor office or clinic 110, and test facility 112. Each facility 104, 108, 110, 112 includes one or more computers that communicate over the network 106 in accordance with well-known network communications protocols, such as the TCP/IP standard and the like, or can be received according to network-specific protocols. The documents being processed by the system 102 are accessible over the network 106 and can comprise conventional text documents, messages to which the documents are attached, images, records (e.g. DICOM formatted medical records), or other digital data communications, such as email messages, data transmissions, voice messages, Web pages, and the like. All such data that are processed by the system 102 will be referred to generally as "documents", except where the context requires a more specific definition.

The computers at each facility 104, 108, 110, 112 can provide the capability of generating documents and messages for transmittal to the other system computers. The documents can be stored at any network location that is accessible to all the computers of the system, such as the document archive 113 illustrated in FIG. 1 that contains documents for processing as described herein. If desired, the ability to store documents into the archival storage 113 for later retrieval can be limited to a particular facility in the system 102. Limiting the ability to manage document archives for the system can be important for improved efficiency of compliance with requirements, such as governmental regulations for patient privacy and the like. Alternatively, all the computers in the system can be given similar capabilities and functionality.

In the FIG. 1 system, the hospital 104 includes an Archive Station 114 and a Web-based Viewer Station 116. The Archive Station is the only computer among the illustrated computers that can store documents into network accessible storage for access by the other computers of the system 102. This functional exclusivity provides a centralized document management responsibility at the hospital that resides in the Archive Station, and any other device at the hospital comprising an Archive Station, for better management of regulatory compliance. Thus, other facilities may have only a single machine on premises that is capable of operating as an Archive Station, or may have multiple machines (with preferably controlled access) that are capable of operating as an Archive Station. The Viewer Station 116 provides a computer work station at which hospital personnel can view system documents from network storage and send and receive messages, and otherwise enjoy full functionality for operations in the system 102, except that the Viewer Station cannot store documents into network storage.

It should be understood that the single block representation 116 of the Viewer Station is for simplicity of illustration only; the hospital 104 can include many Viewer Station computers with the described functionality. Similarly, the Archive Station 114 is illustrated as a single block in FIG. 1, but it should be understood that more than one computer at the hospital 104 can incorporate the Archive Station functionality as described herein. As described further below, the Archive Station 114 will include data storage for documents. The data storage can be in the form of network attached storage, or other high capacity data storage solutions. As noted, the document data storage can be at one of the illustrated locations 104, 108, 110, 112, or can be at a network location 113 that is accessible to all the computers of the system, so long as storage rights are limited to the Archive Station 114 and all other computers have no storage rights.

The system 102 can include other computers with a variety of functionality and capabilities. The FIG. 1 computers are shown as deployed at different facilities for purposes of illustration, but the computers also could be located elsewhere in the system. For example, the Remote Clinic 108 includes a Connect Station 118 that is used for connecting the Remote Clinic to the network document storage 113 and thereby gains viewing rights to documents. The Doctor Office 110 is shown as including another Web-based Viewer Station 120, which will have capabilities like those of the hospital Viewer Station 116. The Test Facility 112 can include a Diagnostic Station 122 that is configured to receive diagnostic and test data from a variety of equipment, such as x-ray machines, CT scanners, workstations, digital image processing equipment, and the like. Any one of the locations 104, 110, 112, 118 can include each one of the station types described, or particular locations can be limited in the type of station (Archive, Viewer, Diagnostic, or Connect) that is installed. As described more fully below, the different station types can be implemented on a wide variety of computers by installation of software that is installed on a computer and that provides the functionality described.

Archive Station Operation

Figure 2:
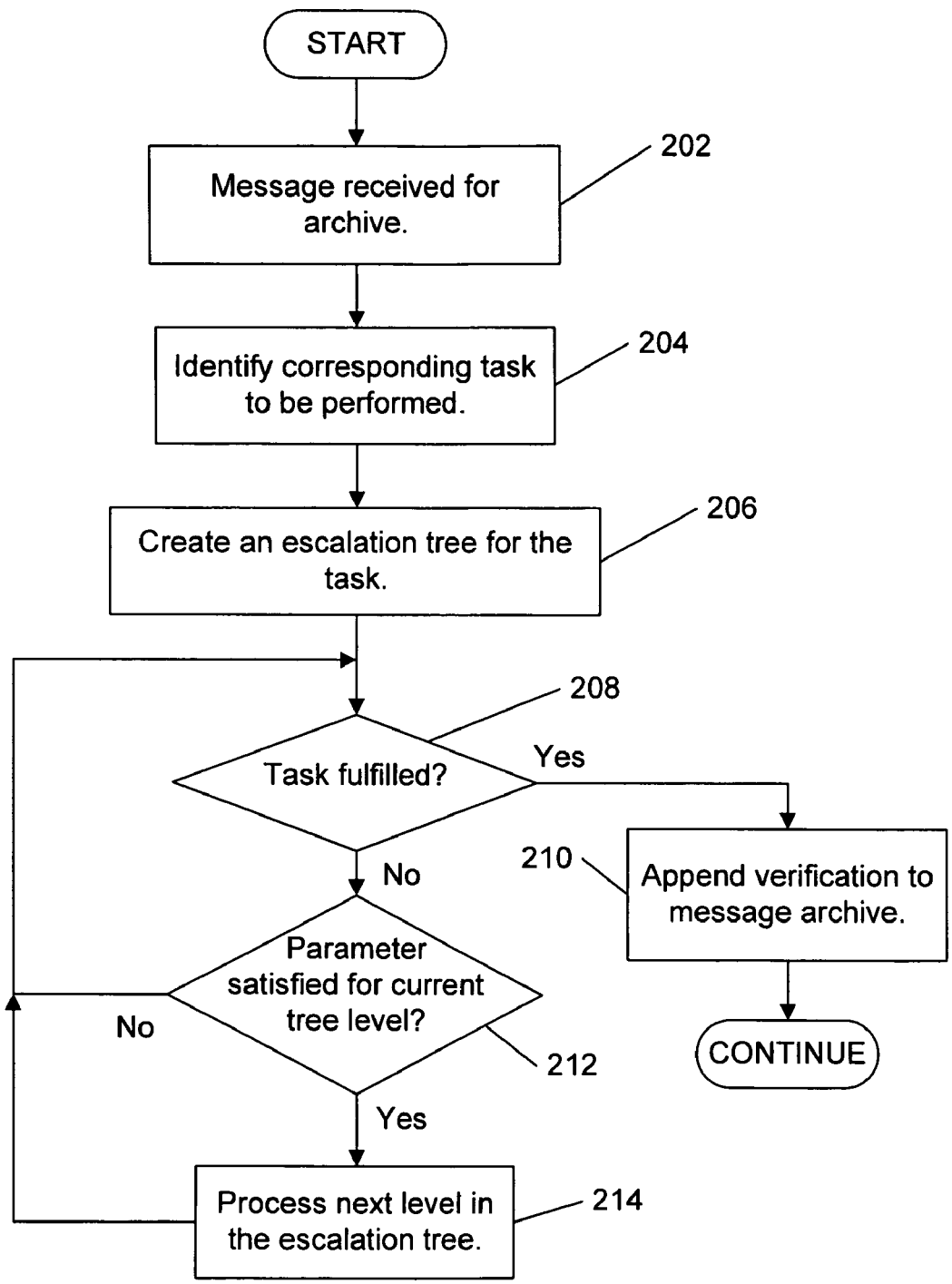
FIG. 2 is a flow diagram that shows the operation of archival operations for a document of the FIG. 1 document processing system.

FIG. 2 illustrates the operation of the Archive Station. In the first operation, represented by the flow diagram box numbered 202, a document is received for the Archival Storage 113 (FIG. 1). In this context, the term "document" refers to a document that is received at the station for archive, such as an electronic document attached to an email message or an electronic document that is received from another computer for storage into the archive 113. Alternatively, the document may comprise an electronic message that itself will be archived. That is, the "document" may be an email message that is to be stored into the archive 113. Storing messages and the like can be important, for example, in the case of messages such as acknowledgement messages or approval messages that must be stored for regulatory compliance or liability reasons. As noted above, storage into the system archive 113 can only be accomplished by means of an Archive Station 114 (FIG. 1).

In the next operation, represented by the box 204, the Archive Station identifies a task to be performed in connection with the received document. The received documents, when stored in the system for later access over the computer network, are placed in network data storage such that each stored document is associated (linked) with a network location and corresponding system data records for processing and management, thereby comprising a document archive, and such that each stored document is associated with one or more tasks. For example, the task associated with a report is that the report must be read. The task that is associated with a study is that the study must be reviewed. Thus, each received document stored into the Archive will be associated with a task that must be performed (fulfilled) for document management purposes.

Next, at block 206, an escalation list is created and is associated with the document archive so as to specify an ordered list of items to be checked until fulfillment of the task. The items are specified in terms of an escalation parameter, independent of the task, that is to be satisfied. For example, the escalation parameter might be specified as units of time, where a time limit is associated with each escalation list item, and the expiration of each time limit will trigger the initiation of the next escalation list item. Thus, the task associated with a document might be for an attending physician to read a report. The escalation list might comprise a list of contacts to be notified of the need for the report to be read, beginning with the attending physician. A typical scenario would be that the escalation list starts with the attending physician mobile telephone number, followed by the physician office telephone number, then an administrative assistant contact number, hospital staff contact number, and so forth.

FIG. 2 shows that after the escalation list is created, the system checks for fulfillment of the task, as indicated by the decision box numbered 208. When the system receives confirmation that the task has been fulfilled, an affirmative outcome at the decision box 208, a verification is appended to the message archive data record (block 210) and system operation then continues. As long as the task remains unfulfilled, a negative outcome at the decision box 208, the system checks to determine if the parameter for the current escalation list item has been satisfied. For example, if the parameter is time, then the system will check to see if the time limit for the current escalation list item has expired. The checking is represented by the decision box 212. If the current escalation tree level has not been satisfied, a negative outcome at the decision box 212, then the system returns to block 208 to wait for an indication that the task has been fulfilled. If the parameter for the current escalation tree level has been satisfied, an affirmative outcome at the decision block 212, then the system processes the next level in the escalation tree and returns to checking for task fulfillment at the decision block 208. The system operation of waiting for task fulfillment and checking for satisfied escalation list parameters can be performed by the Archive Station, or can be performed by a designated computer of the facility, or by some other element of the system 102, as desired, so long as the fulfillment of tasks is communicated to the Archive Station for updating of the document data storage records.

One typical configuration of the system is for the escalation tree to comprise a list of contacts, with a time limit parameter for each of the items of the list. For example, the escalation list might begin with the mobile telephone number for the attending physician. The next list entry might be the office telephone number of the attending physician, followed by a telephone number for an administrative assistant for the physician, then a hospital staff contact number, followed by a messenger email address, and so forth. The time limit parameter for contacting the physician might be thirty minutes, meaning that thirty minutes after the system first checks for task fulfillment (reading of the report), if no task fulfillment has been indicated, then the system will automatically begin checking at the second level of the escalation tree. In this example, the second level corresponds to the physician office telephone number. If the time limit for the second level of the escalation tree is fifteen minutes, then the system will automatically check the third level of the tree if fifteen more minutes pass with no indication of task fulfillment. Thus, each escalation tree level will be associated with a parameter, such as a time limit, and the system will check each escalation tree level for the parameter (such as time limit) to be satisfied before moving to the next level in the tree. Processing of the escalation tree is halted as soon as the associated task is indicated as being fulfilled. Therefore, in the example, checking the time limits for expiration will halt as soon as the system receives an indication that the report has been read by the attending physician.

The last process operation associated with every escalation list can be a default action, such as a request for human intervention that requires a physical acknowledgment action by a human operator for the task to be deemed fulfilled. For example, the last escalation list item can require a human input from a system input/output device such as a keyboard. This helps ensure that otherwise unfulfilled tasks will eventually receive attention and do not go unfulfilled, or otherwise require human involvement. This can help to ensure satisfactory resolution of each task.

Task Identification

Figure 3:
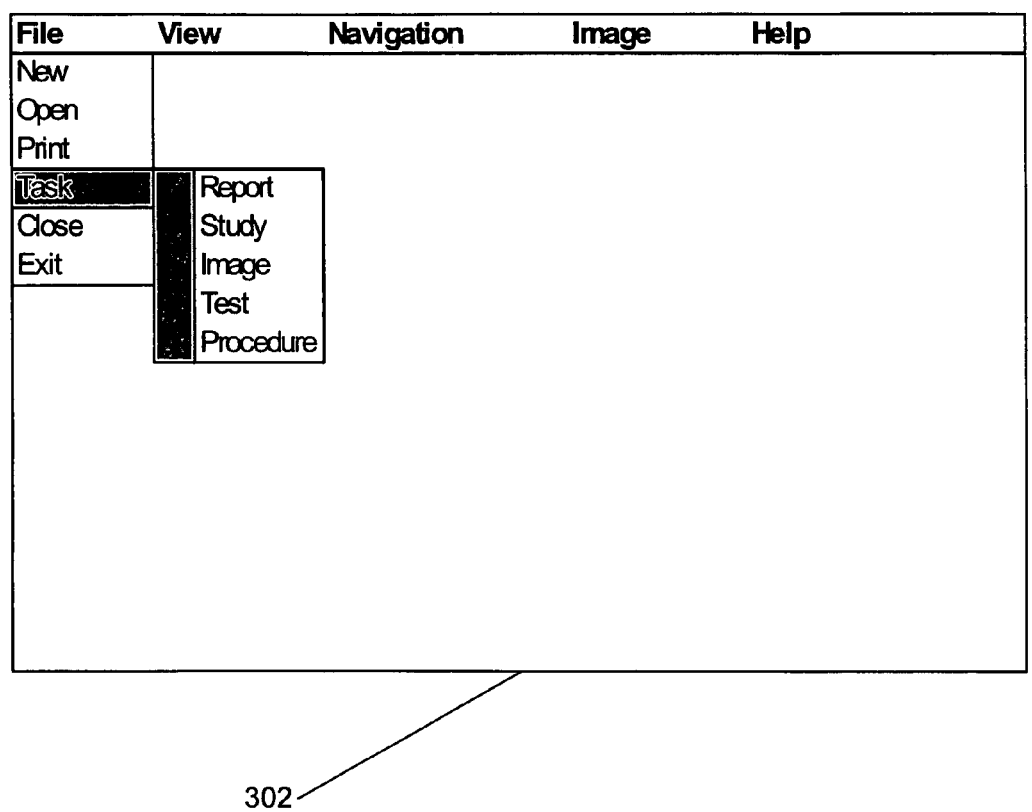
FIG. 3 is a representation of a display screen of the Archive Station in FIG. 1 showing identification of a task for a archive document.

The task identification operation (block 204 in FIG. 2) is preferably performed by an Archive Station operator who works from a user interface that presents a menu providing a list of predetermined tasks that are associated with corresponding documents, as selected by the operator. For example, FIG. 3 is a representation of an application window 302 on a computer display for the Archive Station application software that shows a document being viewed at the Archive Station computer (insignificant details of the document are not illustrated in FIG. 3 for simplicity of illustration). As noted above, a document being processed in FIG. 3 may be a message, an electronic document, images, records, voice messages, Web pages, and other digital data communications.

The "File" menu in FIG. 3 shows a variety of operations that are possible for a document being processed. FIG. 3 shows that, via the File menu item "New", a new file, or document, can be created. Other operations for a document include Print, Close, Exit, and Task. If the "Task" menu item is selected (indicated by dark gray shading in FIG. 3) then a corresponding task identification menu is shown as a drop-down list. This type of user interface will be familiar to those skilled in the art. A task identification menu is a list of document types supported by the system and for which processing operations are possible The task identification menu illustrated in FIG. 3 shows that the document types for the document being processed may comprise either a Report (which will need to be read), a Study (which will need to be reviewed), an Image (which will need to be examined), a Test (which will need to be ordered), or a Procedure (which will need to be initiated). The actual task items of the task identification menu, from which an operator may choose, are preferably selected by an administrator in a system initialization or customization operation of the application. That is, the system is preferably capable of customization so the tasks that can be associated with an archive document can be suitable for the facility in which the system is operating and can be different from the set illustrated in FIG. 3. The task items of FIG. 3 are provided for example only, and the actual list elements can be provided according to a predetermined option list from Which an Archive Station operator makes a selection, or the option list can be customizable for a facility installation by an authorized system administrator.

Document Hierarchy

In the system 102, each document stored in the Archival Storage 113 (FIG. 1) is characterized by a document hierarchy of predetermined data field values. The hierarchy data fields are provided to more precisely identify documents and enable efficient tracking and management of a wide variety of document types and formats. As an example, the documents in the system 102 are characterized by a document hierarchy comprising multiple data fields, such as:

Patient
  Study
    Series
      Image
        Instance.

The indentation levels above are intended to correspond to the ordering, or levels, of the document hierarchy. The hierarchy levels can be mapped onto each stored document. Any one level may contain multiple entries. For example, the topmost hierarchy level may include multiple entries, each entry representing a different patient. Thus, each hierarchy level includes potentially multiple entries and each entry includes potentially multiple instances of succeeding (lower) levels. Thus, each Patient might be associated with multiple Studies, such as an abdominal study, an upper thoracic study, a blood pressure study, an allergenic study, an ophthalmic study, and the like. Different patients might be associated with different sets of studies. A patient might be associated with multiple studies of the same type, such as multiple blood pressure studies. Therefore, the next level in the document hierarchy specifies a study Series, such as a first series blood pressure study, second series blood pressure study, third blood pressure study, and so forth. Each Series may be associated with one or more Images, which is the next hierarchy level. For example, an upper thoracic study might include multiple images from different viewing perspectives or angles, as specified by the patient's physician or a specialist. Finally, each image in a study series might undergo certain revisions or manipulations, and therefore each image can be associated with multiple Instances, which is the last level in the document hierarchy. Such revisions might include, for example, increased contrast applied to the image, or changed color rendition to identify objects of interest. For such revisions, it could be important to maintain the original image, as well as identify the revised image. Each such distinct image will comprise an Instance of a particular Image.

Figure 4:
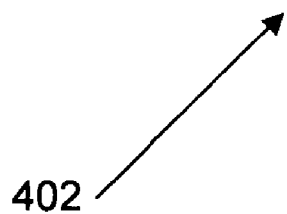
FIG. 4 is a representation of a document hierarchy data structure that is stored in the system illustrated in FIG. 1.

FIG. 4 is a representation of a document hierarchy data structure 402 that is stored in the system Archive 113 illustrated in FIG. 1. The document data structure is associated (linked) with the document in archival storage, and specifies the system document number for the document. As noted above, the other possible data that identifies each document stored in the system includes Patient, Study, Series, Image, and Instance. Exemplary values are provided in FIG. 4 for purposes of illustration.

In particular, the "Patient" level identifies an individual with whom the document is associated. The "Studies" field typically pertains to a particular patient related subject, such as an office visit by the patient, an examination, ailment, occurrence, or body region of interest. The "Series" field typically relates to images that were acquired or obtained at the same time or during a particular examination event. An image series is typically requested by a medical specialist for a particular study and will specify an axis of viewing (front series of images, side series, top, etc.). The "Images" field identifies particular images in a series. The "Instances" field relates to multiple versions or transformed images for a patient. For example, every image for a particular patient has an "Image" identifier for the image, but each image will have associated with it a particular table of Instance values. Thus, if an image is edited or compressed, then the edited or compressed version of the image will have a new instance number. The original image and the compressed image will have the same "Images" field, but will have different "Instance" field values. The images will likely also have the same "Studies" and "Series" field values.

Escalation Tree

Creation of the escalation tree (block 206 in FIG. 2) specifies an order or sequence of notifications that will be pursued to ensure that the corresponding task is fulfilled. The task is considered fulfilled when the one or more operations with which the task is associated are completed, as evidenced by a network event such as data received into the system through an Archive Station. For example, if the identified task corresponds to a Report document, then the task will be deemed fulfilled when the system receives an indication that the Report has been read. If the task corresponds to an Image document, then the task is deemed fulfilled when an indication is received that the Image has been examined. If the task corresponds to a Test, then the task is deemed fulfilled when the Test is ordered. Similarly, each possible task that is defined for the documents stored in the system 102 will have a corresponding operation (or multiple operations) that must be completed for the task to be deemed fulfilled. When the operations for a particular task are indicated as completed, the task is fulfilled, regardless of the completion status of any other task associated with the document or any other document. When a task is fulfilled, the document archive of the associated document is appended with a data record that indicates task fulfillment. The indication can comprise, for example, setting the value of a field in the data archive.

FIG. 5 is a representation of an escalation tree data structure 502 stored in the Archive Station computer 114 (FIG. 1). FIG. 5 shows that the escalation tree data structure includes a data field that references the document number, and preferably includes other information for purposes of patient identification, such as patient name and patient number. The escalation tree can include document data that further identifies the document to which the escalation tree refers, such as the data hierarchy terms described above. For example, FIG. 5 shows that the escalation tree includes document information referred to as "Study 23, Series 1." In the FIG. 5 escalation tree, data values are provided for "Study" and for "Series", but there is no specification of data values for "Images" and "Instances", indicating such fields have no relevance for the document or indicating that default values apply.

The FIG. 5 escalation tree data structure 502 includes an Action column that provides an ordered list of actions to be taken for fulfilling the task (FIG. 3) that is identified with the document. For example, the escalation tree in FIG. 5 indicates that the corresponding document is a report for a patient "John Subject" and therefore the task to be fulfilled involves the patient's doctor (or other medical professional identified in the task) reading the report document. That is, the Archive Station operator who is storing the Report document into system data storage has selected "Report" as the task for this document, and therefore the system will create the escalation tree (block 206 of FIG. 2) and will await acknowledgment from the patient's doctor or other identified professional that the Report has been read.

The escalation tree data structure 502 preferably includes contact data and parameter values for each item in the Action column. In accordance with the example described above, the parameters of the FIG. 5 escalation tree data structure 502 relate to time limits. Other escalation tree parameters can relate to, for example, staffing changes (next shift), system resource levels (number of persons available), reserve staff levels, and so forth.

The escalation tree levels in the Action column of the FIG. 5 data structure 502 indicate that the first operation comprises a call to the physician's mobile telephone. The call can be performed manually by an appropriate facility person, or the call can be automatically performed with a machine-generated message, so long as the attending physician or other appropriate person is notified of the Report document that must be reviewed. The call will be connected to the telephone number entry in the Contact Data column that is adjacent to the Action column entry for "Call mobile phone".

In the illustrated example, FIG. 5 shows the time limit to receive an indication of task fulfillment before escalation to the next level is thirty minutes. When the Report document is reviewed, the reviewer will provide an acknowledgement message and the system will deem the task to be fulfilled. At the same time as the acknowledgment message fulfills the task, it also terminates checking for the expiration time of the current entry for the FIG. 5 escalation tree. FIG. 5 shows that each entry in the escalation tree will be associated with a parameter value, such as expiration time, that can be set by an authorized person at the time of document archival and task initiation.

Thus, if the time specified in the first "Expiration Time" entry passes without an acknowledgment from the called physician, then the system proceeds to the next level in the escalation tree, "call pager". The pager call will be to the number specified in the corresponding entry of "Contact Data" for the pager call. If the expiration time for the pager call expires without fulfillment of the task, then the operation of the next level in the escalation tree ("call business office") is carried out, and again the system waits for task fulfillment until the "call business office" expiration time passes. Each level in the escalation tree will, in turn, be performed as the expiration time for each tree level passes, until fulfillment of the task or operation of the last escalation tree level (i.e., human intervention or other "last resort" action). In general, the "last resort" action is a system default that is automatically initiated upon passing the expiration time of the last level in the escalation tree. The last resort action may, if preferred, be absent from the escalation list data structure, as it can be a default operation that is performed as the last item of every escalation tree. Other details of construction and operation of the escalation tree entries can be dependent on system requirements, as will be understood by those skilled in the art.

The archival operation being performed by the operator (the process initiated by the operations of FIG. 2) will include sending a copy of the Report document to the person identified in the task data. The sending of the document can be performed automatically by the system, or the operator can be prompted to manually perform the task. In the FIG. 5 escalation tree example where the document is a Report, the reading of the Report will be indicated by a return message or by data entry from an appropriate Archive Station operator.

Figure 6:
FIG. 6 is a representation of the FIG. 4 data structure after it has been appended with document handling verification data.

When the task for the document is fulfilled, such as when an acknowledgment for the reading of a Report is received, the data structure for the document is appended with a verification. This updating at the Archive 113 can comprise a network event in response to which the system deems the task to be fulfilled. FIG. 6 shows the document hierarchy data structure for the Report after the patient's attending physician has reviewed the Report document. Thus, FIG. 6 shows that the task history for the document is appended to the document hierarchy data structure 402 (FIG. 4) to result in the illustrated data structure 602, which provides evidence that the document was received into the Archival Storage on a particular day at a particular time (Jan. 1, 2005 at 4:30 pm) and was reviewed by the patient's physician (John Expert, MD) on a particular day at a particular time (Jan. 2, 2005 at 9:15 am). Thus, reporting compliance with regulations and tracking of document status are improved with the operation of the system 102 and the maintenance of the document data structures and escalation tree information as described above.

Computers

As described above, the operations in accordance with the invention can be quickly and efficiently performed by computers that are in communication with the network (see FIG. 1). The operations can be carried out by multiple computers that share the tasks described above, or the tasks can be performed by a single computer having sufficient resources for all the tasks required. For example, a single computer can be configured to have application software installed so as to operate as an Archive Station 114, or the computer can be configured as any one of the other components described above, including the Viewer Station 116, 120; the Connect Station 118; or the Diagnostic Station 122. Alternatively, a single computer could be configured with one or more application software to perform operations corresponding to more than one of the components. In any case, the operations can be performed by the computer as a result of executing installed software programs comprising computer instructions, in conjunction with user input. An example of a suitable computer for performing the operations described above is illustrated in FIG. 7 and is described below.

Figure 7:
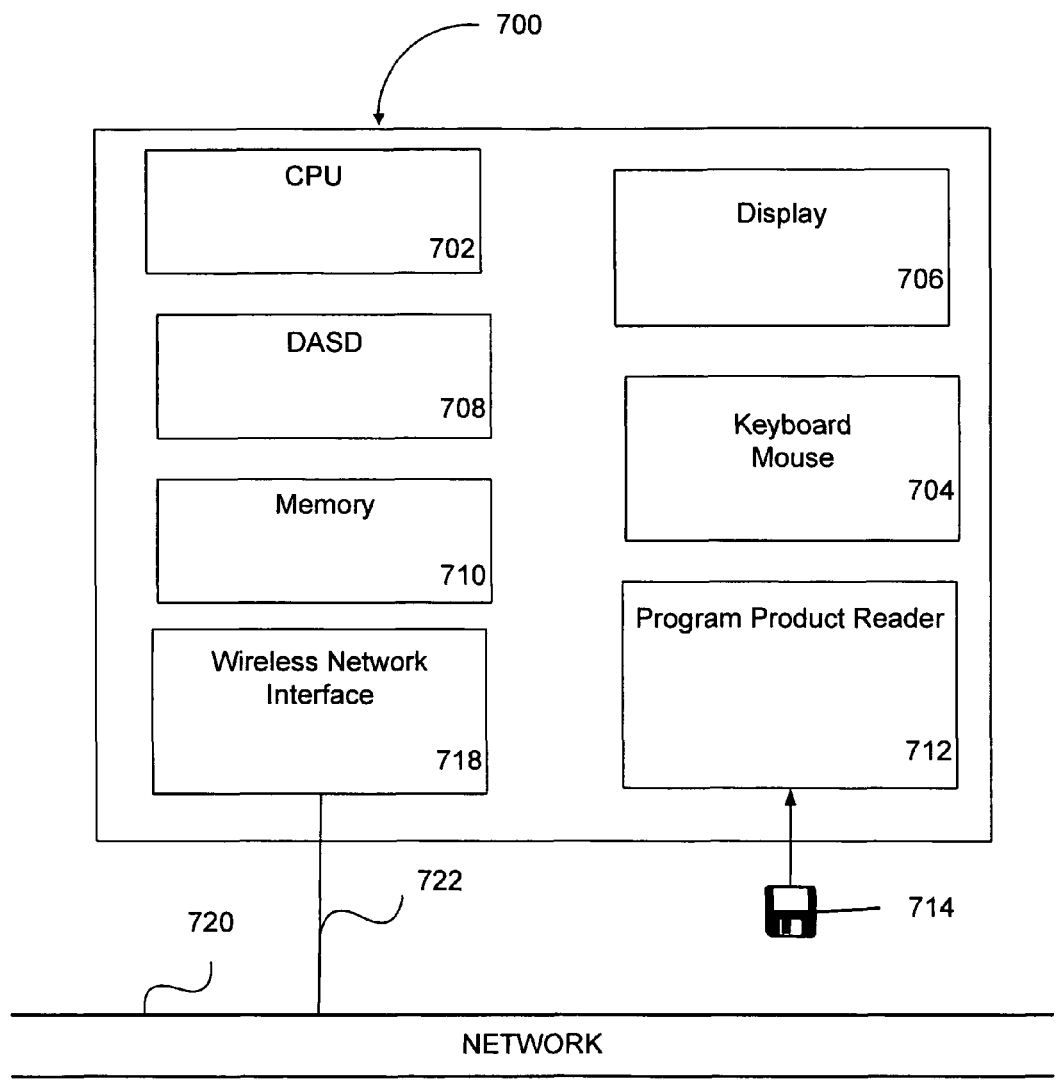
FIG. 7 is a block diagram that illustrates the construction of a computer that performs the operations of the document processing system illustrated in FIG. 1.

FIG. 7 shows an exemplary computer 700 such as might comprise a computer for executing the operations described above. The computer 700 operates in a networked environment that permits communication with other computers. The computer 700 operates under control of a central processor unit (CPU) 702, such as a "Pentium" microprocessor and associated integrated circuit chips, available from Intel Corporation of Santa Clara, Calif., USA. A computer user can input commands and data from a keyboard and computer mouse 704, and can view inputs and computer output at a display 706. The display is typically a video monitor or flat panel display. The computer 700 also typically includes a direct access storage device (DASD) 708, such as a hard disk drive. A memory 710 typically comprises volatile semiconductor random access memory (RAM). Each computer preferably includes a program product reader 712 that accepts a program product storage device 714, from which the program product reader can read data (and to which it can optionally write data). The program product reader can comprise, for example, a disk drive, and the program product storage device can comprise removable storage media such as a magnetic floppy disk, a CD-R disc, a CD-RW disc, or DVD disc.

The computer 700 can communicate with any other computers, if networked, over a computer network 720 (such as the Internet or an intranet) through a network interface 718 that enables communication over a connection 722 between the network 720 and the computer. The network interface 718 typically comprises, for example, a Network Interface Card (NIC) or a modem that permits communications over a variety of networks.

The CPU 702 operates under control of programming instructions that are temporarily stored in the memory 710 of the computer 700. When the programming instructions are executed, the computer performs its functions. Thus, the programming steps implement the functionality of the system described above. The programming steps can be received from the DASD 708, through the program product storage device 714, or through the network connection 722. The program product storage drive 712 can receive a program product 714, read programming steps recorded thereon, and transfer the programming steps into the memory 710 for execution by the CPU 702. As noted above, the program product storage device can comprise any one of multiple removable media having recorded computer-readable instructions, including magnetic floppy disks and CD-ROM storage discs. Other suitable program product storage devices can include magnetic tape and semiconductor memory chips. In this way, the processing steps necessary for operation in accordance with the invention can be embodied on a program product.

Alternatively, the program steps can be received into the operating memory 710 over the network 720. In the network method, the computer receives data including program steps into the memory 710 through the network interface 718 after network communication has been established over the network connection 722 by well-known methods that will be understood by those skilled in the art without further explanation. The program steps are then executed by the CPU 702 thereby comprising a computer process.

Thus, the invention provides techniques for event notification verification and escalation of network documents. The techniques, applicable in a variety of document processing systems, improves the efficiency and appropriateness of document handling.

The present invention has been described above in terms of a presently preferred embodiment so that an understanding of the present invention can be conveyed. There are, however, many configurations for network document processing not specifically described herein but with which the present invention is applicable. The present invention should therefore not be seen as limited to the particular embodiments described herein, but rather, it should be understood that the present invention has wide applicability with respect to network document processing generally. All modifications, variations, or equivalent arrangements and implementations that are within the scope of the attached claims should therefore be considered within the scope of the invention.

We claim:

1. A method of processing documents accessed over a computer network, the method comprising:
   storing one or more documents in a network data storage, wherein each document of the documents is associated with a document archive;
   specifying a task to be performed that is associated with each stored document, wherein the task is selected from a group consisting of reading a report, reviewing a study, examining an image, ordering a test, and initiating a procedure;
   creating an escalation tree that is associated with the document archive and that specifies ordered levels of notifications to be pursued until fulfillment of the task, wherein each escalation tree level is attempted in order to receive confirmation that the task has been fulfilled;
   determining whether a parameter associated with a current escalation tree level has been satisfied;
   performing process operations associated with a next escalation tree level if the parameter associated with the current escalation tree level has been satisfied;
   determining whether the task is fulfilled;
   halting the determining and performing process operations if the task is determined to be fulfilled; and
   appending a verification of task fulfillment to the document archive,
   wherein the task is determined to be fulfilled when a predetermined network event has occurred,
   wherein the predetermined network event comprises a change to at least one parameter in the document archive,
   wherein the change to at least one parameter identifies the fulfilled task and a person responsible for fulfilling the task and a date and time of fulfillment, and
   wherein a last process operation associated with the escalation tree is a request for human intervention that requires a physical acknowledgment action by a human operator to be deemed fulfilled.

2. The method as defined in claim 1, wherein the predetermined network event comprises receipt of a network verification message.

3. A method as defined in claim 1, wherein the escalation list includes contact data for each escalation tree level.

4. A method as defined in claim 1, wherein the stored document can be any one of a plurality of document formats.

5. A method as defined in claim 4, wherein the document formats include image data.

6. A method as defined in claim 1, wherein the document archive includes a plurality of hierarchy fields that characterize document content, and the hierarchy fields include Patient, Study, Series, Image, and Instance identification fields.

7. A computer processing system that processes documents accessed over a computer network, the system comprising:
   a memory;
   a network communications interface that permits communications between the computer processing system and the network; and
   a document processor coupled to the network communication interface, wherein the document processor is configured with software instructions to perform steps comprising:
      storing one or more documents in a network data storage, wherein each document of the documents is associated with a document archive;
      specifying a task to be performed that is associated with each stored document, wherein the task is selected from a group consisting of reading a report, reviewing a study, examining an image, ordering a test, and initiating a procedure;
      creating an escalation tree that is associated with the document archive and that specifies ordered levels of notifications to be pursued until fulfillment of the task, wherein each escalation tree level is attempted in order to receive confirmation that the task has been fulfilled;
      determining whether a parameter associated with a current escalation tree level has been satisfied;
      performing process operations associated with a next escalation tree level if the parameter associated with the current escalation tree level has been satisfied;
      determining whether the task is fulfilled;
      halting the determining and performing process operations if the task is determined to be fulfilled; and
      appending a verification of task fulfillment to the document archive,
   wherein the document processor is configured with software instructions to perform further steps comprising:
      determining that the task is fulfilled when a predetermined network event has occurred
   wherein the predetermined network event comprises a change to at least one parameter in the document archive,
   wherein the change to at least one parameter identifies the fulfilled task and a person responsible for fulfilling the task and a date and time of fulfillment, and wherein a last process operation associated with the escalation tree is a request for human intervention that requires a physical acknowledgment action by a human operator to be deemed fulfilled.

8. The system as defined in claim 7, wherein the predetermined network event comprises receipt of a network verification message.

9. A system as defined in claim 7, wherein the escalation tree includes contact data for each escalation tree level.

10. A system as defined in claim 7, wherein the stored document can be any one of a plurality of document formats.

11. A system as defined in claim 10, wherein the document formats include image data.

12. A system as defined in claim 7, wherein the document archive includes a plurality of hierarchy fields that characterize document content, and the hierarchy fields include Patient, Study, Series, Image, and Instance identification fields.

13. A computer processing system that processes documents accessed over a computer network, the system comprising:
   a processor; a memory;
   means for storing one or more documents in a network data storage, wherein each document of the documents is associated with a document archive;
   means for specifying a task to be performed that is associated with each stored document, wherein the task is selected from a group consisting of reading a report, reviewing a study, examining an image, ordering a test, and initiating a procedure;
   means for creating an escalation tree that is associated with the document archive and that specifies ordered levels of notifications to be pursued until fulfillment of the task, wherein each escalation tree level is attempted in order to receive confirmation that the task has been fulfilled;
   means for determining whether a parameter associated with a current escalation tree level has been satisfied;
   means for performing process operations associated with a next escalation tree level if the parameter associated with the current escalation tree level has been satisfied;
   means for determining whether the task is fulfilled;
   means for halting the determining and performing process operations if the task is determined to be fulfilled; and
   means for appending a verification of task fulfillment to the document archive,
   wherein the task is determined to be fulfilled when a predetermined network event has occurred,
   wherein the predetermined network event comprises a change to at least one parameter in the document archive,
   wherein the change to at least one parameter identifies the fulfilled task and a person responsible for fulfilling the task and a date and time of fulfillment, and
   wherein a last process operation associated with the escalation tree is a request for human intervention that requires a physical acknowledgment action by a human operator to be deemed fulfilled.

14. A system as defined in claim 13, wherein the predetermined network event comprises receipt of a network verification message.

15. A system as defined in claim 13, wherein the escalation tree includes contact data for each escalation tree level.

16. A system as defined in claim 13, wherein the document archive includes a plurality of hierarchy fields that characterize document content, and the hierarchy fields include Patient, Study, Series, Image, and Instance identification fields.

17. A computer-readable storage medium having instructions stored thereon that, when read by a computer, cause the computer to perform operations for processing documents accessed over a computer network, the operations comprising:
   storing one or more documents in a network data storage, wherein each document of the documents is associated with a document archive;
   specifying a task to be performed that is associated with each stored document, wherein the task is selected from a group consisting of reading a report, reviewing a study, examining an image, ordering a test, and initiating a procedure;
   creating an escalation tree that is associated with the document archive and that specifies ordered levels of notifications to be pursued until fulfillment of the task, wherein each escalation tree level is attempted in order to receive confirmation that the task has been fulfilled;
   determining whether a parameter associated with a current escalation tree level has been satisfied;
   performing process operations associated with a next escalation tree level if the parameter associated with the current escalation tree level has been satisfied;
   determining whether the task is fulfilled;
   halting the determining and performing process operations if the task is determined to be fulfilled; and
   appending a verification of task fulfillment to the document archive,
   wherein the task is determined to be fulfilled when a predetermined network event has occurred,
   wherein the predetermined network event comprises a change to at least one parameter in the document archive,
   wherein the change to at least one parameter identifies the fulfilled task and a person responsible for fulfilling the task and a date and time of fulfillment, and
   wherein a last process operation associated with the escalation tree is a request for human intervention that requires a physical acknowledgment action by a human operator to be deemed fulfilled.

18. The computer-readable storage medium as defined in claim 17, wherein the predetermined network event comprises receipt of a network verification message.

19. The computer-readable storage medium as defined in claim 17, wherein the escalation list includes contact data for each escalation tree level.

20. The computer-readable storage medium as defined in claim 17, wherein the stored document can be any one of a plurality of document formats.

21. The computer-readable storage medium as defined in claim 20, wherein the document formats include image data.

22. The computer-readable storage medium as defined in claim 17, wherein the document archive includes a plurality of hierarchy fields that characterize document content, and the hierarchy fields include Patient, Study, Series, Image, and Instance identification fields.

* * * * *